(12) United States Patent
Gonzalez Trotter

(10) Patent No.: US 7,020,240 B2
(45) Date of Patent: Mar. 28, 2006

(54) METHOD AND APPARATUS FOR MEASURING MATTER PROPERTIES

(75) Inventor: Dinko Eduardo Gonzalez Trotter, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 222 days.

(21) Appl. No.: 10/750,394

(22) Filed: Dec. 31, 2003

(65) Prior Publication Data

US 2005/0147209 A1    Jul. 7, 2005

(51) Int. Cl.
*G01N 23/06* (2006.01)

(52) U.S. Cl. .............................. 378/53; 378/4; 378/62; 382/132

(58) Field of Classification Search ................ 378/4, 378/8, 15, 53, 62; 382/131, 132; 250/363.02–363.04
See application file for complete search history.

(56) References Cited

U.S. PATENT DOCUMENTS

| | | | |
|---|---|---|---|
| 6,633,626 B1 | 10/2003 | Trotter et al. | |
| 6,674,835 B1* | 1/2004 | Kaufhold et al. | 378/53 |
| 2003/0072409 A1* | 4/2003 | Kaufhold et al. | 378/53 |
| 2003/0147491 A1* | 8/2003 | Gonzalez Trotter et al. | 378/22 |
| 2003/0215057 A1 | 11/2003 | Trotter et al. | |

* cited by examiner

*Primary Examiner*—David V Bruce
(74) *Attorney, Agent, or Firm*—Jean K. Testa; Christian G. Cabou

(57) ABSTRACT

Embodiments of methods, apparatuses, devices, and/or systems for determining matter properties are described.

26 Claims, 2 Drawing Sheets

METHOD AND APPARATUS FOR MEASURING MATTER PROPERTIES

STATEMENT REGARDING FEDERALLY SPONSORED RESEARCH & DEVELOPMENT

The U.S. Government may have certain rights in this invention pursuant to Contract No. 22287 MDA-9050-0-10041 awarded by the US Office Of Naval Research and Henry M. Jackson Foundation.

BACKGROUND

This disclosure is related to techniques for evaluating or measuring matter properties, such as evaluating density from imagery, for example.

Radiological imaging, such as X-ray imaging, for example, may be used to create images of a human subject or their organs and extremities, for example. One particular application of X-ray imaging may be for early detection of breast cancer, which represents a significant cause of mortality among women in the United States. Currently, one of the more widespread screening techniques for breast cancer is X-ray mammography, where malignancies may be detected based on shape and or radiological density. However, current techniques and/or devices used for early detection of breast cancer and/or determination of breast cancer risk may produce varying results, based on one or more factors, such as the subjective analysis of a physician, differing results obtained by differing imaging methods, and equipment variations from imaging device to imaging device. A need exists, therefore, for a method and/or apparatus to improve consistent accuracy of radiological imaging.

BRIEF DESCRIPTION OF THE DRAWINGS

Subject matter is particularly pointed out and distinctly claimed in the concluding portion of the specification. The claimed subject matter, however, both as to organization and method of operation, together with objects, features, and advantages thereof, may best be understood by reference of the following detailed description when read with the accompanying drawings in which:

DETAILED DESCRIPTION

Figure 1:
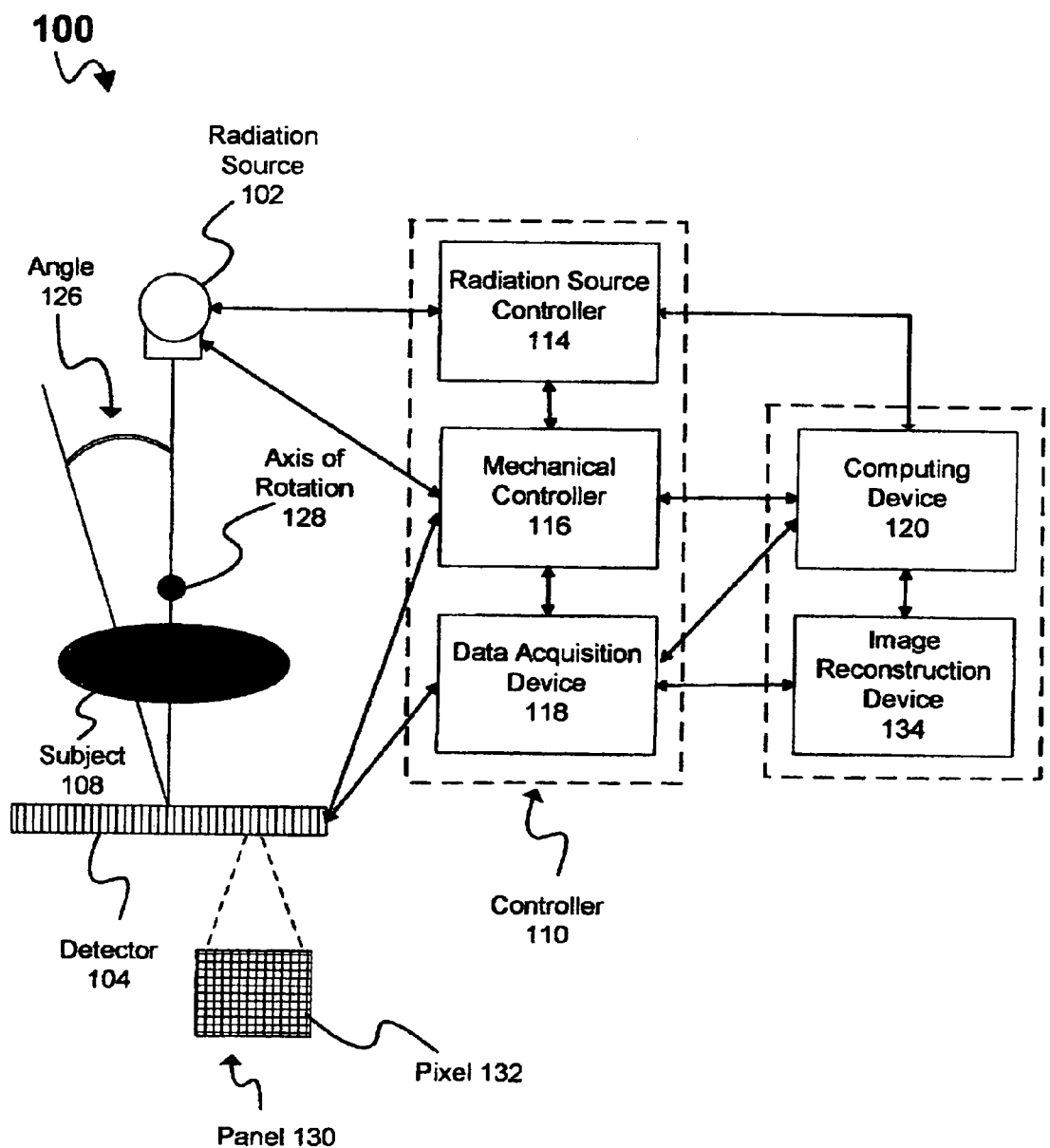
FIG. 1 is a schematic diagram of one embodiment of an imaging system.

In the following detailed description, numerous specific details are set forth to provide a thorough understanding of the claimed subject matter. However, it will be understood by those skilled in the art that the claimed subject matter may be practiced without these specific details. In other instances, well-known methods, procedures, components and/or circuits have not been described in detail so as not to obscure the claimed subject matter.

Radiological imaging, such as X-ray imaging, for example, has become a useful tool for medical applications, although it is worthwhile to note that numerous non-medical applications exist, and the claimed subject matter is not limited in this respect. One particular medical us for this type of imaging may be for early detection of cancer. Malignancies may be detected based at least in part on density and/or morphological features. Here, the term density refers to radiological density, such as glandular and/or fatty tissue composition on a percentage basis, for example, although other types of density may alternatively be measured or employed depending on the particular context. Imaging techniques, such as X-ray imaging, provide a non-invasive technique for detecting the presence of cancerous cells within a human subject, for example. As alluded to previously, breast cancer is a significant concern, and early detection may increase a patient's chances of survival and/or lengthen their period of effective treatment. However, detection of malignancies in breast tissue is complex and challenging for a variety of reasons. The human breast is complex from a radiological perspective. Furthermore, current techniques for interpreting an x-ray image are dependent, at least partially, on the subjective judgment of a physician. Currently, a physician will typically visually evaluate the density of a breast from an X-ray mammogram, and will typically classify the image in a quartile scale, correlating to breast tissue density. He or she may then use this information to assess breast cancer risk. Factors that may affect the visual perception of density, therefore, may include the subjective judgment of a physician, variations among imaging devices, and/or variations among imaging techniques employed. For example, the geometry of the object being X-rayed may affect the resultant image, such as by altering the X-ray path length, and thereby inducing photon scatter, for example. Additionally, equipment variations, such as X-ray filter variation and electronic drift, may also affect the resultant image. Therefore, differing results may be obtained depending at least in part on the judgment of the physician, the imaging device utilized, and/or the geometry of the object to be X-rayed, for example. Thus, a technique for determining object density based at least in part on one or more radiological images, wherein the technique may more accurately and/or objectively determine tissue density, and account for one or more of the aforementioned factors, may be desirable for at least one or more of the reasons stated previously.

One particular imaging technique that may be used in medical imaging is tomosynthesis. Tomosynthesis refers to a technologically advanced variation of two-dimensional imaging, where a representative three-dimensional image may be constructed based at least in part on a plurality of two-dimensional images, which may comprise digital images based on one or more sets of data acquired through application of relatively low doses of X-rays, in at least one embodiment. In this particular embodiment, an X-ray source and/or an X-ray detector may take various positions, such as in an articulated manner, with reference to an object, such as a human breast, for example. A series of images, which may be referred to as views, may be obtained, such as a series of views of a particular object obtained from differing angles of incidence. In one embodiment, the constructed or reconstructed image of a single view may be referred to as a slice, and multiple slices may be employed to construct a three-dimensional image of the object, for example.

Referring now to FIG. 1, there is provided a schematic diagram of an embodiment of an imaging system. Illustrated in FIG. 1 is an imaging system embodiment 100, which may comprise an embodiment of a tomosynthesis system, for example. System 100 comprises at least one radiation source 102, which may comprise an X-ray source, although it is desirable to note that other radiation sources, such as sources producing one or more types of penetrating photons, may be used in alternate embodiments. In one particular embodiment, radiation source 102 may comprise a source capable of producing X-ray spectra, such as a 26 kV 100 mAs Rhodium filtered beam with a Rhodium anode, for example. However, the claimed subject matter is not limited in this respect. Filter materials suitable for use in an imaging system such as just described may include Molybdenum, Rhodium, Copper and/or Aluminum, as just a few examples. Additionally, anode materials may include Molybdenum, Rhodium or Tungsten, as just a few examples. However, system 100 further comprises a detector 104, which may comprise a detector array, for example. The detector may have an additional detector device (not shown), such as a scintillator, which may provide one or more functions to aid the detector in detecting x-rays, for example. The detector device may have a particular material thickness, and may comprise a plate form factor, in at least one embodiment. Additionally, the detector may have a detector cover (not shown), which may, for example, protect one or more detector components, such as the one or more additional detector devices or one or more detector panels from contamination, as just an example. The detector cover may additionally have a particular material thickness, and may have a form factor similar to the one or more additional detector devices, for example. The detector may comprise a series of panels, such as panel 130, wherein each panel has a plurality of pixels, such as pixel 132, for example, which are typically employed to detect photons, such as those emitted from a scintillator that has been excited by X-rays. For example, although not shown in detail, pixels of detector 104 may comprise photosensors, such as photodiodes, and may include the capability to detect incident light based at least in part on the charge it produces across the diodes, for example. For example, in one embodiment, X-rays incident upon a scintillator may produce light photons capable of being detected by the pixels of detector 104. Of course, this is just one example of an embodiment of a radiation imaging device and many more are possible and included within the scope of the claimed subject matter.

Radiation source 102 and/or detector 104 may be at least partially controlled by a controller 110. Controller 110 may comprise a radiation source controller 114, a mechanical controller 116 and a data acquisition device 118. Additionally, a computing device 120 may be employed to exchange electronic data with one or more components of controller 110, for example, and, additionally, an image reconstruction device 134 may additionally be employed as part of system 100. In one embodiment, image reconstruction device 134 may be embodied with computing device 120 as part of a single platform, denoted by a dashed line in FIG. 1, for example. Reconstruction device 134 may comprise software executing on a computing platform, but, of course, this is just one possible embodiment. Additionally, it is again noted that the foregoing imaging system is merely one particular embodiment of an imaging system and the claimed subject matter is not limited in scope to this particular system.

In operation, system 100 may obtain one or more radiological images of object 108 in the following manner, although, it is noted that this is just one embodiment, and the claimed subject matter is not so limited. Radiation source controller 114 may provide signals, such as timing and/or control signals, to radiation source 102, driving it to emit radiation for a particular period of time. Radiation source 102 may, depending at least in part on the type of radiation source, produce a stream of relatively high energy photons, which may comprise a conical stream of photons, substantially directed towards object 108, for example. Depending on factors, such as the matter density of object 108 and/or the angle of incidence 126, high energy photons may be scattered, attenuated, or absorbed, for example. At least a portion of the high energy photons may strike a scintillator, in this embodiment, thereby producing, by excitation, additional light photons capable of being detected by detector 104. Thus, at least a portion of the pixels of detector 104 may obtain a particular photon count or pixel intensity, and, typically, more dense regions of the object provide greater attenuation, and may result in a reduced photon count for each representative pixel. The obtained image may be referred to as a pixel-wise image, as a pixel represents a portion of the image, for example. The pixels of detector 104 may produce digital data based at least in part on the photon count, for example, and at least a portion of the data acquired by detector 104 may be provided to data acquisition device 118. The resulting pixels may comprise a digital image representation of object 108, for example, and may be referred to as a measured signal, in at least one embodiment. At least a portion of the data may be provided to imaging reconstruction device 134 and/or computing device 120, for example, which, as stated previously, may comprise devices resident on a single computing platform, for example.

In this embodiment, if differing images, or views, are to be obtained, a mechanical controller, such as 116 in FIG. 1, may cause radiation source 102 and/or the detector 104 to rotate about axis 128, for example, which may result in a change in the angle of incidence 126. Of course, the claimed subject matter is not limited in scope to this particular technique for obtaining another view or to this particular imaging system. Many other approaches are possible within the scope of the claimed subject matter. One or more additional images may be obtained by performing one or more of the aforementioned functions, and the desired number of additional images obtained may depend on factors such as, for example, the complexity of the object, the type of radiation source, and/or the complexity of the imaging system, for example. Image reconstruction device 134 and/or computing system 120 may at least partially construct a digital image representation, such as a slice, from a single view, and may, additionally, construct a three-dimensional digital image representation from one or more two-dimensional slices obtained by the imaging system, for example. Technology to construct a three-dimensional digital image from slice views is well-known and, therefore, will not be discussed herein detail in order to conserve space. However, it is noted that, in one alternative embodiment, computing device 120 may perform one or more image construction functions, such as high speed image reconstruction, for example, or other types of special purpose image reconstruction. The reconstructed image may be stored on a mass storage device (not shown), which may comprise a memory device embodied on image reconstruction device 134 or computing device 120, for example, but which may b removable. Additionally, although not illustrated in detail, computing device 120 may comprise one or more microprocessors, one or more memory devices, one or more input/output ports, and/or a user interface, such as a graphical user interface (GUI), for example. Additionally, image reconstruction device 134 may comprise a special purpose computing device, or may comprise software executing on a computing device, for example. The user interface may be utilized to provide one or more instructions to portions of imaging system 100, for example, via computing device 120. Additionally, an output device, such as an LCD screen, as one example, may be used to at least partially display the image, for example. Again, this is merely one particular embodiment and the claimed subject matter is not limited in scope to this particular embodiment.

As stated previously, imaging, such as X-ray imaging, may be used to enable a determination of matter density or other properties, for example. A radiological representation of an image, simply stated, may result at least in part from unattenuated photons passing through an object, which may be referred to as direct events, as well as scattered photons, which may scatter into a substantially opposed detector by being deflected by the object being imaged, for example. As previously discussed, creation of such a representation may, but does not necessarily, include use of scintillator as an intermediary in the process to permit capture of the relevant information by a detector, such as 104. Image density may be correlated to the amount of photons unattenuated, as denser materials may tend to result in greater attenuation in photons. Scattering of photons may be related to the angle of incidence between a radiation source and an object, and to one or more properties of the object, such as shape and/or density, for example. Numerous techniques exist for estimating or eliminating scatter, and, by use of one or more of these techniques, scatter may be substantially taken into account, which may improve image accuracy, for example, as explained in more detail below.

As stated previously, current imaging analysis techniques may incorporate one or more subjective factors, one or more physical factors and/or one or more electronic factors into the determination of the density of an object from an X-ray image. Although the claimed subject matter is not limited in scope to a particular technique or embodiment, one or more factors tending to reduce the accuracy of radiological imaging may be accounted for, thereby increasing the effectiveness of imaging, for uses including medical imaging. In one particular embodiment, for example, a radiological image, such as an X-ray image, may be acquired for an object, such as a human breast. In this embodiment, the object may have a particular thickness t, and may be partially compressed by use of a compression paddle, although this is not a requirement. The object may have a substantially uniform thickness, although, again, this is not a requirement and objects of a non-uniform thickness are likewise contemplated. The image data of the object may, for example, be obtained by a digital imaging system, in this particular embodiment, and may be defined as $I_j$, where j represents an individual pixel of image data for a detector comprising a plurality of pixels, for example. $I_j$, therefore, may comprise a representation of photons incident on a particular pixel. The acquisition of an image, I, comprising a plurality of $I_j$, may be obtained by a system, such as system 100 of FIG. 1, and may comprise a measured signal, such as a measure of signal intensity or a representation thereof. Of course, it is worthwhile to note that the claimed subject matter is not so limited. Therefore, any method of imaging wherein an image representation of properties, such as density, is obtained for at least a portion of an object may be used in at least one embodiment. However, continuing with this example, in this embodiment, the acquired image may be represented by the pixel data for at least a portion of the pixels j of a detector device, such as detector 104 of FIG. 1. Therefore, for one particular embodiment, the obtained image may be modeled by a relationship as follows:

$$I_j = b_j + s_j = I_j^o e^{-\mu'_j t} + s_j \quad [1]$$

where $b_j$ is a signal attributable to unattenuated photons, and $s_j$ is a signal attributable to scattered photons. In this embodiment, scattered photon signal $s_j$ may be estimated ($s_j'$), and subtracted from $I_j$, in the following manner $$I_j' = I_j - s_j' \quad [2]$$

This results in the calculation of $I_j'$, which, in this embodiment, represents an approximated scatter reduced signal. The estimate of scatter may be based on one or more well-known scatter correction techniques, but any method whereby scatter may be at least partially determined or reduced may be used in at least one embodiment. One particular method of at least partially determining scatter, which may be employed by at least one embodiment, is set forth in the following patent application, "Scatter Correction Method for Non-Stationary X-Ray Acquisitions", Publication No. US 2003/0215057 A1, application Ser. No. 10/063,806, filed May 15$^{th}$, 2002, by González Trotter et al., assigned to the assignee of the presently claimed subject matter, although it is worthwhile to note that the claimed subject matter is not so limited, and any suitable method for at least partially determining scatter may be employed, in at least one embodiment. Of course, in an alternative embodiment, the effects of scatter may not be accounted for, and may be included as part of the technique. In one embodiment, for example, a scatter correction technique may be incorporated, whereby the technique is constructed to account for the scatter which may be inherent in the type of imaging technique and/or the type of object being imaged, for example. In such an approach, one or more modulation factors may be utilized to account for at least a portion of the photons detected by one or more pixels of the detector attributable at least in part to scatter.

In this embodiment, an additional or second radiological image may be obtained, using a substantially similar technique to the technique previously described, but without the object in place, for example. Again, similarly to the previous approach, the amount of scattered photons $s_j^o$ may be estimated and a resultant estimated scatter reduced image may be obtained by subtracting the estimated scatter signal $s_j^{o'}$ for each $I_j^o$, in the following manner $$I_j^{o'} = I_j^o - s_j^{o'} \quad [3]$$

In this embodiment, $I_j^{o'}$ may be referred to as a scatter-reduced open geometry image. Obtaining an additional image utilizing a similar technique but without the subject in place may result in the quantification of one or more equipment related factors, as these factors may be repeatable and/or inherent in the equipment and/or technique used to obtain the particular images, for example. Therefore, obtaining a second image and mathematically modifying the data obtained from the first imaging process based at least in part on the data obtained in the second imaging process may result in at least partially removing equipment related factors, such as electronic drift and filter variations, and other factors, from the image data. The resultant image, referred to as an approximated scatter reduced open geometry image, is represented by $I_j^{o'}$, where j varies over the entire image in this particular embodiment.

Using at least a portion of the data obtained in the two images $I_j'$ and $I_j^{o'}$, a mean attenuation coefficient, $\mu'_j$, may be obtained for each pixel j, where t represents the nominal thickness of the object for which at least one of the images is obtained. In this embodiment, the mean attenuation coefficient, in this context, refers to a mean numerical value of attenuation determined for an associated pixel, for example. This may, for example, comprise a numerical data value, where the numerical data value is based, at least in part, on at least two radiological data sets, where the data sets account for one or more random or pseudo-random factors affecting radiological results, for example. Thus, the mean attenuation coefficient may be determined in accordance with the following relationship:

$$\mu_j^t = \frac{\ln I_j^{0\prime} - \ln I_j^\prime}{t} \quad [4]$$

Solving for $\mu_j^t$, the mean attenuation coefficient for each representative pixel j may be obtained. This value may at least partially represent the attenuation attributable to an object, and, therefore, may be used to at least partially determine matter density, as explained hereinafter. In addition, if, for example, the thickness of the subject is known in greater detail, such as on a pixel by pixel basis, for example, the thickness t for equation 4 may be substituted by $t_j$, the thickness for each representative pixel. Likewise, it is noted that similar adaptations of the prior and foregoing relationships to take into account various additional parameters, depending on the particular context, are possible and included within the scope of the claimed subject matter.

In this embodiment, it may also be desirable to model the behavior of imaging data for one or more objects of known matter composition, shape, etc. For example, with knowledge of a source photon spectrum S(E), knowledge of typical attenuation behavior and attenuation coefficients for differing types of matter as a function of photon energy, such as fatty material and glandular material, which, in this context, may comprise material categorized substantially by radiological density, for example, fatty material may be radiologically less dense than glandular material, although this is not a requirement. In this embodiment, fatty material and glandular material are represented here by ($\mu_f(E)$) and ($\mu_g(E)$), respectively, theoretical imaging intensity models may be constructed for both the object image and open geometry image, $I_j^{(m)}$ and $I_j^{o(m)}$, respectively. Thus, theoretical expressions for these modeled intensities using the previously described information are as follows:

$$I_j^{0(m)} = \sum_{l=1}^{M} S(E_l) e^{-\mu_c(E_l)t_c} (1 - e^{-\mu_d(E_l)t_d}) E_l \quad [5]$$

$$I_j^{(m)} = \sum_{l=1}^{M} S(E_l) e^{-\mu_c(E_l)t - \mu_c(E_l)t_c} (1 - e^{-\mu_d(E_l)t_d}) E_l \quad [6]$$

Here, the attenuation coefficient, and thickness of the detector cover material of the detector cover, are denoted by $\mu_c$ and $t_c$, respectively. The theoretical mean attenuation coefficient for each pixel j, for an object of nominal thickness t, photon spectrum S(E), and a selected matter density may, therefore, be obtained by $$\mu_j^{t(m)} = \frac{\ln I_j^{0(m)} - \ln I_j^{(m)}}{t} \quad [7]$$

By use of this obtained theoretical mean attenuation coefficient, and a calculated mean attenuation coefficient for an object, as discussed above in connection with imaging system 100, a percentage composition of an object, such as percentage glandular composition and/or percentage fatty composition, may be obtained for a pixel j, in the following manner $$C_j = 100 \cdot \left(1 - \frac{\mu_j^{g(m)} - \mu_j^t}{\mu_j^{g(m)} - \mu_j^{f(m)}}\right) \quad [8]$$

where $\mu_j^{g(m)}$ and $\mu_j^{f(m)}$ are the theoretically-calculated mean attenuation coefficients for an object made of 100% glandular and 100% fat tissue, respectively. Of course, as previously suggested, it may be appropriate to make adaptations of the prior set of relationships to reflect additional parameters that may be present, depending on the particular context. It is intended to include all such adaptations within the scope of the claimed subject matter. In this particular embodiment, by use of the foregoing technique, or an adaptation thereof, a pixel-by-pixel density composition of an object, represented by $C_j$, may be obtained, which may be referred to as an attenuation map, in at least one embodiment, because, for example, of the pixel-wise determination of composition. It is noted that the resulting data is substantially operator independent, substantially imaging device independent, substantially imaging technique independent, substantially object thickness independent, etc.

By utilizing one or more of the foregoing relationships, or an adaptation thereof, an image may also be constructed which represents a mean attenuation coefficient image. This image may be formed as a two dimensional image configuration, or may be formed as a three-dimensional image configuration, for example. In at least one embodiment, the resultant mean attenuation coefficient image may be used to determine object density, such as breast tissue density, substantially independent of one or more factors tending to affect accuracy, as explained previously.

Figure 2:
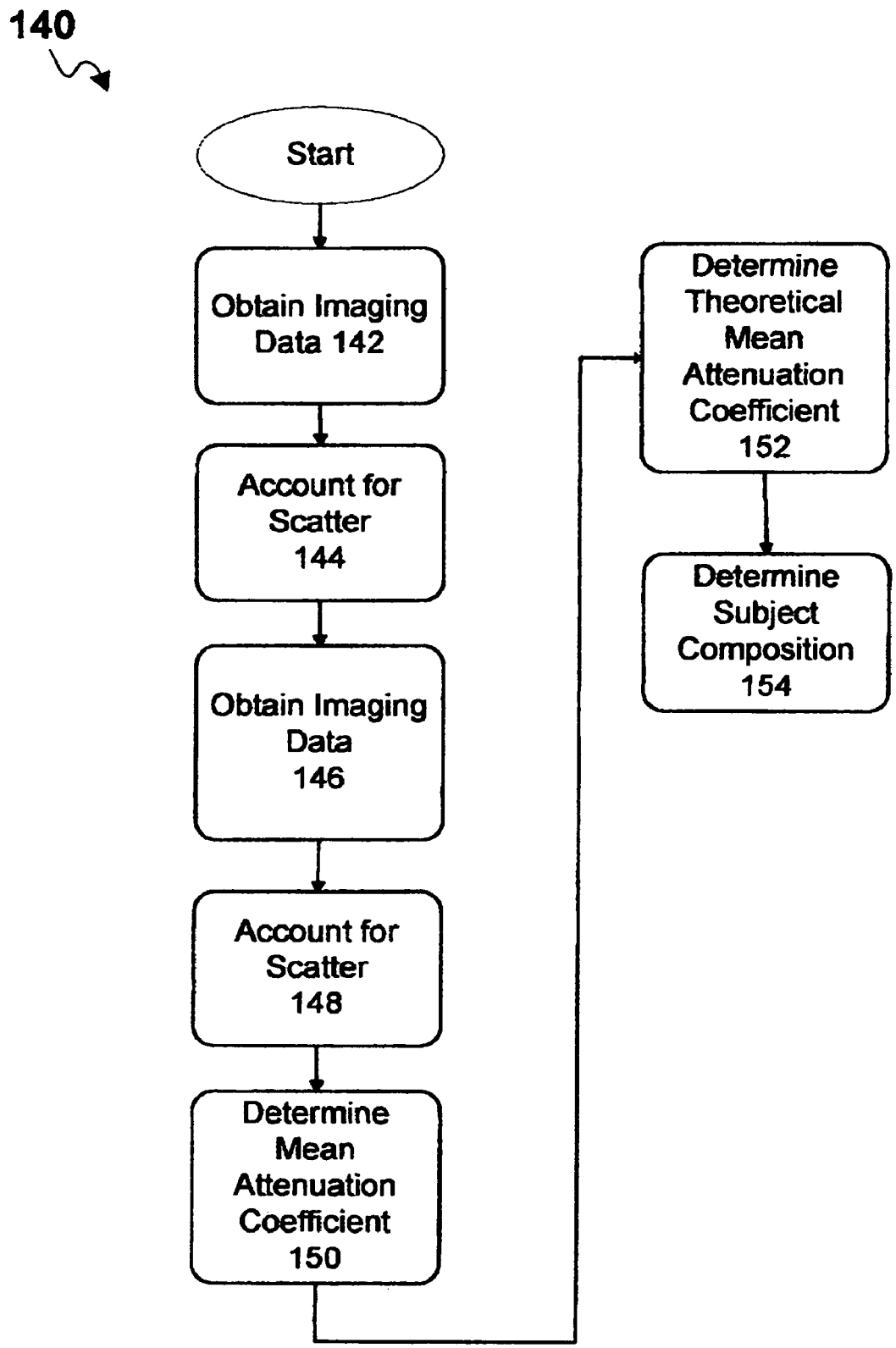
FIG. 2 is a flowchart illustrating one embodiment of a technique for measuring matter properties.

Referring now to FIG. 2, one embodiment of a technique for constructing such images is illustrated by a flowchart, although, of course, the claimed subject matter is not limited in scope in this respect. Thus, such an embodiment may be employed to at least partially form a mean attenuation coefficient image, as described below. The flowchart illustrated in FIG. 2 may be used to substantially perform one or more imaging operations of an imaging system, such as system 100 of FIG. 1, for example, although th claimed subject matter is not limited in this respect, and the order in which the blocks are presented does not necessarily limit the claimed subject matter to any particular order. Likewise, intervening additional blocks not shown may be employed and without departing from the scope of the claimed subject matter.

Flowchart 140 depicted in FIG. 2 may in alternative embodiments be implemented in software, hardware and/or firmware, and may comprise discrete operations. In this embodiment, imaging data for a subject may be obtained for a plurality of pixels of an imaging system at block 142. Scatter may be accounted for at block 144, such as by one or more scatter correction techniques, as previously described, for example. At block 146, imaging data, without an object, may be obtained for a plurality of pixels of such an imaging system and, similarly, scatter may be accounted for at block 148. At block 150, the mean attenuation coefficient may be determined, for the plurality of pixels, such as by one or more of the foregoing methods, for example. At block 152, one or more modeled imaging intensities may be obtained for one or more types of matter, and utilized to determine a theoretical mean attenuation coefficient for the plurality of pixels. At block 154, the composition of the object, which may be based on a percentage composition, may be determined for the plurality of pixels, and a representative image comprising percentage composition may be formed. As stated previously, this may be a two-dimensional or a three-dimensional image, for example, or, alternatively, may comprise a single value representing an approximate composition, such as XX% fatty tissue and YY% glandular tissue, in the case of a breast image, for example. In this embodiment, one or more coefficients may be averaged for example, to obtain a single percentage value representing the object, for example, although many other approaches to represent the data obtained may be employed or devised and remain within the scope of the claimed subject matter.

It is, of course, now appreciated, based at least in part on the foregoing disclosure, that software may be produced capable performing one or more of the above-described operations. It will, of course, also be understood that, although particular embodiments have just been described, the claimed subject matter is not limited in scope to a particular embodiment or implementation. For example, one embodiment may be in hardware, such as implemented to operate on a device or combination of devices, as previously described, for example, whereas another embodiment may be in software. Likewise, an embodiment may be implemented in firmware, or as any combination of hardware, software, and/or firmware, for example. Likewise, although the claimed subject matter is not limited in scope in this respect, one embodiment may comprise one or more articles, such as a storage medium or storage media. This storage media, such as, one or more CD-ROMs and/or disks, for example, may have stored thereon instructions, that when executed by a system, such as a computer system, computing platform, or other system, for example, may result in an embodiment of a method in accordance with the claimed subject matter being executed, such as one of the embodiments previously described, for example. As one potential example, a computing platform may include one or more processing units or processors, one or more input/output devices, such as a display, a keyboard and/or a mouse, and/or one or more memories, such as static random access memory, dynamic random access memory, flash memory, and/or a hard drive, although, again, the claimed subject matter is not limited in scope to this example.

In the preceding description, various aspects of the claimed subject matter have been described. For purposes of explanation, specific numbers, systems and/or configurations were set forth to provide a thorough understanding of the claimed subject matter. However, it should be apparent to one skilled in the art having the benefit of this disclosure that the claimed subject matter may be practiced without the specific details. In other instances, well-known features were omitted and/or simplified so as not to obscure the claimed subject matter. While certain features have been illustrated and/or described herein, many modifications, substitutions, changes and/or equivalents will now occur to those skilled in the art. It is, therefore, to be understood that the appended claims are intended to cover all such modifications and/or changes as fall within the true spirit of the claimed subject matter.

What is claimed is:

1. A method of determining one or more matter properties, comprising:
    determining, at least in part, a mean attenuation coefficient for said matter using a plurality of radiological data sets;
    comparing said mean attenuation coefficient with a theoretical mean attenuation coefficient; and
    determining one or more matter properties, based at least in part on said comparison.

2. The method of claim 1, wherein said matter comprises one or more of: glandular matter and fatty matter.

3. The method of claim 2, wherein said one or more matter properties comprises radiological density in terms of percentage of glandular and/or fatty matter.

4. The method of claim 3, wherein said plurality of radiological data sets comprises at least two radiologically produced images.

5. The method of claim 4, wherein said density is determined on a pixel-by-pixel basis.

6. The method of claim 3, wherein said mean attenuation coefficient comprises a numerical data value, wherein said numerical data value is based, at least in part, on at least two radiological data sets wherein the data sets account for one or more random or pseudo-random factors affecting results.

7. The method of claim 6, wherein said one or more random or pseudo-random factors affecting results comprise one or more of: photon scatter, matter shape, matter size, and variations in equipment measuring the radiological data.

8. The method of claim 3, wherein said plurality of radiological data sets comprises at least two radiologically produced images;
    said theoretical mean attenuation coefficient being based, at least in part, on a mathematical model of image data.

9. The method of claim 8, wherein said mathematical model accounts for one or more of: photon spectrum, attenuation factors for said glandular and fatty matter as a function of photon energy, and response behavior of a detector.

10. A method of determining a property of a material, comprising:
    obtaining a first radiological data set for at least a portion of said material by use of an imaging system;
    obtaining a second radiological data set by use of said imaging system without said material;
    determining, at least partially, a mean attenuation coefficient, by using at least a portion of said first and said second radiological data set.

11. The method of claim 10, and further comprising:
    at least partially determining a theoretical mean attenuation coefficient, and determining, at least partially, a property of said material, based at least in part on said theoretical mean attenuation coefficient, and said mean attenuation coefficient.

12. The method of claim 11, wherein said material comprises glandular matter and fatty matter and said property comprises glandular and/or fatty matter composition.

13. The method of claim 12, wherein said density is determined from said imaging system on a pixel-wise basis.

14. The method of claim 12, wherein said mean attenuation coefficient on a pixel-wise basis, represented by $\mu^t_j$, where j is a particular pixel, is substantially in accordance with the following relationship $$\mu^t_j = \frac{\ln I^{o\prime}_j - \ln I'_j}{t}$$

where $I'_j$ comprises a first representation of signal intensity at pixel j with scatter at least partially accounted for, $I^{o\prime}_j$ comprises a second representation of signal intensity at pixel j with scatter at least partially accounted for, and t is thickness of said material.

15. The method of claim 12, wherein said theoretical mean attenuation coefficient is determined on a pixel-wise basis, represented by $\mu^{t(m)}_j$, where j is a particular pixel, is substantially in accordance with the following relationship $$\mu_j^{t(m)} = \frac{\ln I_j^{0(m)} - \ln I_j^{(m)}}{t}$$

where, $I_j^{(m)}$ and $I_j^{o(m)}$ comprise a first and second modeled value of signal intensity at pixel j and are obtained by the following relationships $$I_j^{0(m)} = \sum_{l=1}^{M} S(E_l) e^{-\mu_c(E_l) t_c} (1 - e^{-\mu_d(E_l) t_d}) E_l$$

$$I_j^{(m)} = \sum_{l=1}^{M} S(E_l) e^{-\mu_c(E_l) t - \mu_c(E_l) t_c} (1 - e^{-\mu_d(E_l) t_d}) E_l$$

where S(E) comprises a source photon spectrum, and ($\mu_f(E)$) and ($\mu_g(E)$) represent attenuation coefficients for said fatty material and glandular material as a function of photon energy, the attenuation coefficient, and the thickness of the cover material of the detector, are denoted by $\mu_c$ and $t_c$, respectively, and the attenuation coefficient and the thickness of the detector material are denoted by $\mu_d$ and $t_d$, respectively.

16. The method of claim 12, and further comprising determining a percentage glandular and/or fatty matter composition of at least a portion of said material, based at least in part on the ratio of said mean attenuation coefficient and said theoretical mean attenuation coefficient, substantially by application of the following relationship $$C_j = 100 \cdot \left(1 - \frac{\mu_j^{g(m)} - \mu_j^{t}}{\mu_j^{g(m)} - \mu_j^{f(m)}}\right)$$

where $C_j$ comprises a density composition of said subject, $\mu_j^{g(m)}$ and $\mu_j^{f(m)}$ comprise the theoretically-calculated mean attenuation coefficients for an object made of 100% glandular tissue and 100% fatty tissue, respectively.

17. The method of claim 10, wherein said data sets comprise radiologically produced images.

18. An imaging system, comprising:
a detector array, having a plurality of pixels;
a computer coupled to said detector array, said computer configured to, in operation;
obtain a first radiological data set from said detector for at least a portion of an object being imaged;
obtain a second radiological data set from said detector without said object being imaged;
determine a mean attenuation coefficient for one or more of said pixels of said detector;
determine a theoretical mean attenuation coefficient for one or more pixels of said detector for said object being imaged; and
determine a material property of said object for one or more of said pixels of said detector, based at least in part on said mean attenuation coefficient and said mean theoretical attenuation coefficient.

19. The imaging system of claim 18, wherein said imaging system comprises a tomosynthesis system.

20. The imaging system of claim 18, wherein said material property comprises percentage density.

21. The imaging system of claim 18, wherein said object comprises one or more of: glandular matter and fatty matter.

22. The imaging system of claim 18, wherein said object comprises a human breast.

23. An article comprising: a storage medium, having stored thereon instructions, that, when executed, result in the at least partial determination of a material property for an object by:
obtaining a first radiological data set for at least a portion of said material by use of an imaging system;
obtaining a second radiological data set by use of said imaging system without said material; and
determining, at least partially, a mean attenuation coefficient, by using at least a portion of said first and said second radiological data set.

24. The article of claim 23, wherein said instructions, when executed, further at least partially determining a theoretical mean attenuation coefficient, and determining, at least partially, a property of said material, based at least in part on said theoretical mean attenuation coefficient, and said mean attenuation coefficient.

25. The article of claim 24, wherein said material comprises glandular matter and fatty matter and said property comprises glandular and/or fatty matter composition.

26. The article of claim 24, wherein said material property is determined from said imaging system on a pixel-wise basis.

* * * * *